United States Patent [19]

Morimoto et al.

[11] 4,455,225

[45] Jun. 19, 1984

[54] ROTARY LIGHT TESTER FOR CONTINUOUSLY INSPECTING EMPTY CANS

[75] Inventors: Kenji Morimoto, Tokyo; Masato Ashina, Yokosuka, both of Japan

[73] Assignee: Toyo Seikan Kaisha, Ltd., Tokyo, Japan

[21] Appl. No.: 472,219

[22] Filed: Mar. 9, 1983

Related U.S. Application Data

[63] Continuation of Ser. No. 256,333, Apr. 22, 1981, abandoned.

[30] Foreign Application Priority Data

Jun. 18, 1980 [JP] Japan .................................. 55-81378

[51] Int. Cl.³ ........................................... B07C 5/344
[52] U.S. Cl. .................... 209/588; 209/903; 209/905; 209/913; 250/223 R; 250/237 R; 356/240
[58] Field of Search ............... 209/588, 524, 526, 643, 209/903, 905, 919, 644, 538, 558; 250/223 R, 223 B, 237 R; 356/240, 237; 354/277; 198/438, 441

[56] References Cited

U.S. PATENT DOCUMENTS

| Re. 29,891 | 1/1979 | Phillips | 356/237 |
|---|---|---|---|
| 2,812,061 | 11/1957 | Pfister | 209/643 |
| 3,395,285 | 7/1968 | Scanlon et al. | 250/219 |
| 3,416,659 | 12/1968 | Linderman et al. | 209/588 |
| 3,750,877 | 8/1973 | Dvacho et al. | 209/588 |
| 3,991,882 | 11/1976 | Fahnestock et al. | 209/588 |
| 4,034,929 | 7/1977 | Ebner, Jr. | 354/277 |
| 4,074,809 | 2/1978 | McMillin et al. | 209/588 |
| 4,105,122 | 8/1978 | Flood et al. | 209/588 |
| 4,305,816 | 12/1981 | Flood et al. | 209/588 |

Primary Examiner—Robert B. Reeves
Assistant Examiner—Donald Hajec
Attorney, Agent, or Firm—Jordan and Hamburg

[57] ABSTRACT

A rotary light tester for continuously inspecting empty cans discriminates between good cans and defective ones by judging the amount of transit light entering the interior of the empty cans. The light seal circular plate and the freely-reciprocative slide pusher which rotates with the continuous rotating star wheel face each other sandwiching each can receiving seat therebetween. The nozzle opening of the tip of the slide pusher vacuously holds the bottom end of an uncoated or unprinted bright can received in the can receiving seat one by one when the can enters into the empty can supply station just after the trimming. Then, in the light detection station, the opening end of the can is inserted into a groove of the light seal circular plate having a black non-luster surface to further the reflection attenuation of outer entry light, a trap is disposed in the deepest portion thereof, and a conical introduction arrangement makes it easy to insert the opening end therein by advance pushing of the slide pusher.

7 Claims, 9 Drawing Figures

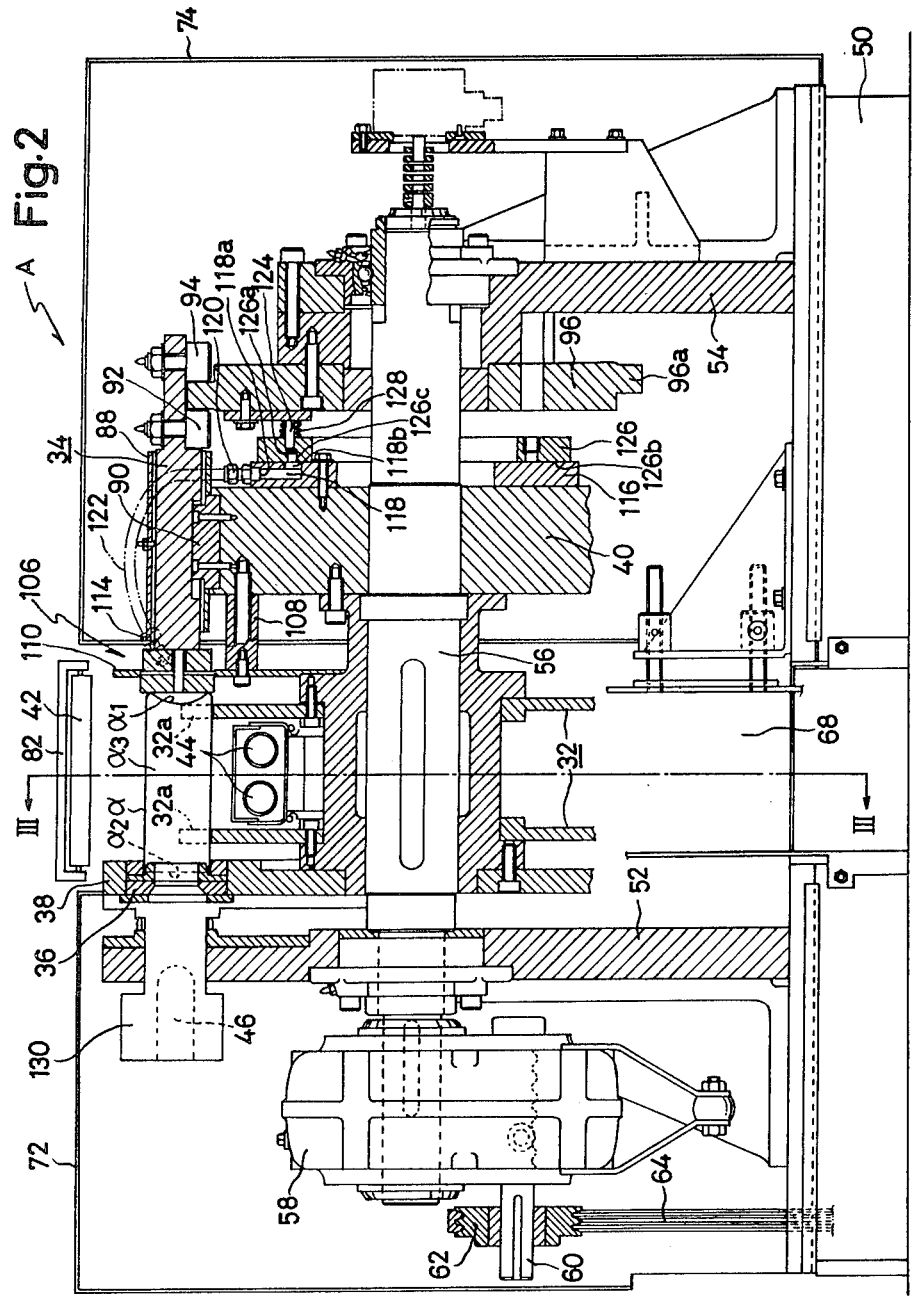

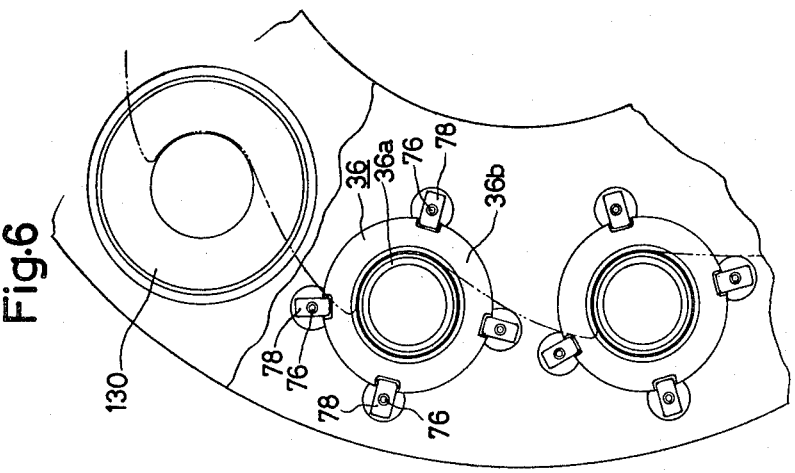
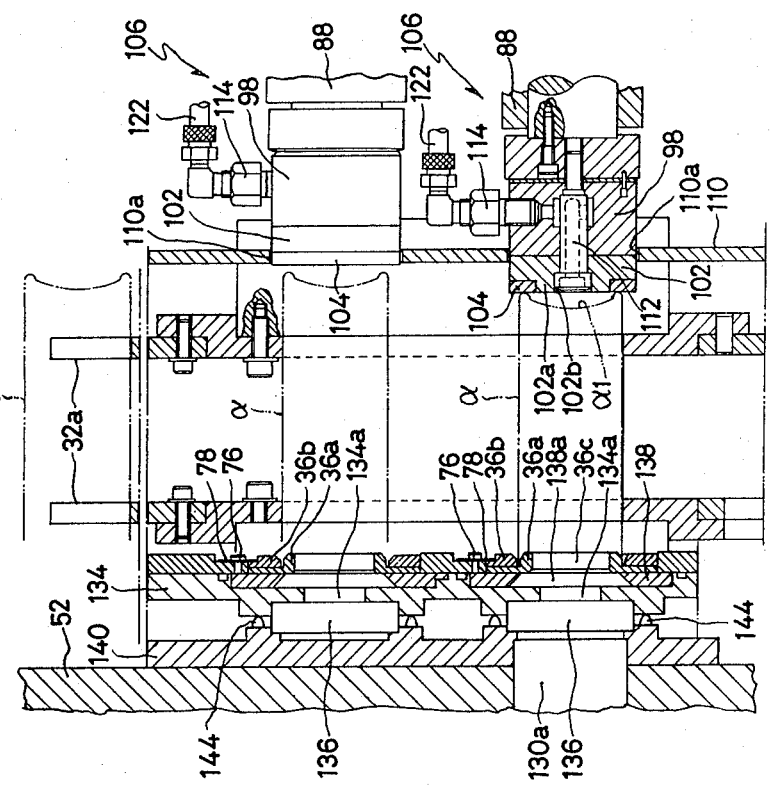

ROTARY LIGHT TESTER FOR CONTINUOUSLY INSPECTING EMPTY CANS

This application is a continuation of application Ser. No. 256,333, filed Apr. 22, 1981, now abandoned.

BACKGROUND OF THE INVENTION

This invention relates to a rotary light tester for inspecting empty cans for defects, and in particular for continuously inspecting empty cans for various defects such as a pinhole and cracks without damaging the cans. Such defects generally result in leakage and occur in the manufacturing line for drawing and ironing can bodies (DI can) of a two-piece can.

This kind of inspection of an empty DI can has heretofore been performed after coating or printing of the inner and outer surface thereof to prevent corrosion and decorate the can after the trimming operation which shears the open end to a fixed finish height Then the necking and flange is formed on the open end. Therefore the amount of transit light in a pinhole of 100μ diameter or below covered with coatings or print inks has been reduced to that in a pinhole of about 10μ diameter. The amount of transit light in a pinhole of 20μ diameters or below cannot be detected with any detection accuracy. Accordingly the detection of very small pinholes is very difficult. Also the accurate detection of defective cans is very difficult owing to the luminuous intensity of the transit light which becomes much less weak upon reaching the light detector with the inner coating film affecting the absorbing attenuation action of the reflective scattered light respectively.

This conventional pinhole detection apparatus is known in U.S. Pat. No. 3,416,659. According to a schematic representation of FIG. 1, a flange opening end (10a) of the DI can (10) tightly contacts a light seal plate (14) of a dark box (12) with the DI can (10) standed upside down. The box (12) has a window (12a) and communicates with the interior of the can (10) through the window (12a). A vacuum pump (not shown) reduces the internal pressure of the box (12) and the can (10) through an exhaust opening (16) provided in a side wall of the box (12), resulting in a difference between the internal and the atmospheric pressure. The can end tightly contacts the flange opening end (10a) of the can (10) with the light seal plate (14). The light seal plate (14) is opaque rubber packing. The bite of the flange opening end (10a) in the light seal plate seals light. The can (10) has light sources (18) around itself and receives both the direct light from the sources (18) and the reflected light from a cylindrical reflector (20) around the source. A photo detector (22) provided within the dark box (12) detects irradiated light through the can (10) from the light sources (18) and then converts irradiated light into an electrical output (24) through a signal circuit (not shown), so that pinholes in the can are found.

According to the conventional apparatus of FIG. 1, light from the light sources (18) passing through the pinhole into the interior of the can (10) reaches the photo detector (22) directly or reaches it with light repeatedly scattered and reflected within the inside wall of the can (10). The photo detector (22) is capable of detecting pinholes anywhere in the can (10) by the optical integral action of reflected, scattered light, and possibly acquires the high sensitive pinhole detection action.

However, in this conventional apparatus, light leakage out of the seal portion between the flange opening end (10a) of the can (10) and the light seal plate (14) produces detection noise. To reduce the amount of light leakage, reduced internal pressure is provided within the box (12) and the can (10) is made to tightly contact the flange opening end (10a) with the light seal plate (14). As a result, wear of the light seal plate (14) become extreme. Generally, in the conventional apparatus, the can (10) receives the light detection action with the condition that the flange is formed in the flange opening end (10a), in other words, the end surface of the flange opening end (10a) is rounded. But even with this roundness the flange opening end (10a) results in extreme wear of the conventional light seal plate (14) of rubber packing. In general, a side use of two to three weeks and both sides use of about six weeks results in frequent replacements of the parts, and makes maintenance of the detection apparatus difficult. In addition, the use of the easily worn light seal plate (14) results in error detection.

Also, in the conventional apparatus, in the same way as regards the air pressure method, coatings or print inks cover pinholes on the inside and outside surfaces of the can. Especially, detecting pinholes of 100μ diameter or less becomes extremely difficult. Practically, a can having pinholes covered with coatings or print inks keeps good air tightness for only a few days. But, in most cases, pinholes produce leakage after a week and remarkably increase the ratio of defective cans. In particular, the defective cans having substances have a practical influence on common consumers. This is a very big problem.

As will be apparent from the above description, it is better to detect pinholes before the coating or printing. But as is well known, in the DI processing operations, the ironing and drawing processed DI can has a necking and flange processing in the opening end. The shape of bright cans remains as it was before the flange processing is made. The trimmed end surface has a width of about 0.17 mm, which is very thin. As a result, when the opening end (10a) tightly contacts the light seal plate (14), the light seal plate (14) has remarkable wear or is easily damaged in a particular case. Therefore, it is impossible to detect pinholes before coating or printing.

Can pinhole detection apparatus described in Japanese Patent Public Disclosure No. 50-48983 and U.S. Pat. No. 3,750,877 and Utility Public Disclosure No. 53-118685 adopt a gasket of opaque material of rubber substances which is the same as the material of the light seal plate (14) of FIG. 1, and consists of a feed star wheel disposed in an empty can supply station, a central star wheel feeding empty cans from the supply station into a light detection station and a discharge star wheel which receives tested cans from the central star wheel located between a defective can discharge station and a good can discharge station. The mechanism and structure of such apparatus is large. In the discharge of good cans, the cans are mechanically held by a yoke opened and closed with actuation of a cam mechanism, and released to the discharge star wheel by actuation of the cam opening the yoke when the held cans come into the good can discharge station. In the discharge of defective cans, cans are mechanically held by the yoke and released by another cam action opening the yoke with a solenoid operation receiving a delay command signal. Thus, holding empty cans by the yoke easily produces holding scars on an outer surface of the empty can and may deteriorate the quality of the cans. Further it is difficult to maintain and check the apparatus.

An apparatus for optically inspecting can bodies, which is described in Japanese Patent Public Disclosure No. 53-12682, (U.S. Pat. No. 4,074,890) adopts elastic forming plastic having an inward ⊐-shaped section, such as a hermetical ring of neoprene or urethane instead of the light seal plate (14) of FIG. 1. In the window (12a) of the box (12) of FIG. 1, a window glass of transparent acrylic resin is hermetically disposed. When the empty can (10) come into the light detection station, the action of atmospheric pressure on the hermetical ring hermetically closes light by pushing the flange (10a) of the can (10) with one piece of the ring on the side of the opening end of the can (10). Therefore, it is inevitable to use the air actuator. It makes the structure mechanically complicated. The position of the flange opening end of the can to the hermetical ring must be strictly determined. If not, leakage of air pressure breaks the light-tightness and produces error judgements, as does abrasion of the hermetical ring. In addition, the air push of a piece of the hermetical ring to the can flange substantially covers the flange end. Hence it is impossible to optically detect cracks of the flange opening end.

The instant invention, therefore, has as an object to provide a rotary light tester for continuously inspecting empty cans which improves defect detection as compared to conventional apparatus.

The object of this invention is to provide a rotary light tester for continuously inspecting empty cans in which the inspection is made on empty cans just after being passed from the trimming work.

Another object of this invention is to provide a rotary light tester for continuously inspecting empty cans in which the inspection is made on bright empty cans before the inner and outer surfaces of the cans are coated or printed.

Another object of this invention is to provide a rotary light tester for continuously inspecting empty cans in which the inspection is made on empty cans before being fed into the necking and the flanging operation.

A further object of this invention is to provide a rotary light tester for continuously inspecting empty cans which makes it possible to precisely detect defective cans without attenuating transit light into the interior of the empty can.

A further object of this invention is to provide a rotary light tester for continuously inspecting empty cans which is supplied with a wear resisting light seal circular plate which is easily maintained and which has a long replacement life.

A further object of this invention is to provide a rotary light tester for continuously inspecting empty cans which is supplied with a light seal circular plate making easy insertion of the opening end of the can.

A still further object of this invention is to provide a rotary light tester for continuously inspecting empty cans which is supplied with a light seal plate which is a circular plate making it easy to coaxially settle the center position of the opening end.

A still further object of this invention is to provide a rotary light tester for continuously inspecting empty cans which is supplied with a light seal circular plate having a groove to insert the opening end of the can therein and being of a material harder than that of the can.

A still further object of this invention is to provide a rotary light tester for continuously inspecting empty cans which is supplied with a light seal circular plate having a groove which is specifically formed to further provide reflective attenuation of outer invasion light.

A still further object of this invention is to provide a rotary light tester for continuously inspecting empty cans which is supplied with a light seal circular plate having a surface which is especially useful to further reflective attenuation of outer invasion of light.

An additional object of this invention is to provide a rotary light tester for continuously inspecting empty cans which is supplied with a star wheel making it smooth to slide freely and receive and discharge cans to a can receiving seat setting empty cans.

An additional object of this invention is to provide a rotary light tester for continuously inspecting empty cans which makes it possible to detect pinholes of $25\mu$ diameter or below with high accuracy.

The above and other advantages of the invention will become more apparent in the following description and the accompanying drawings.

BRIEF DESCRIPTION OF THE DRAWINGS

FIG. 2 is a partial, vertical, schematic, sectional view of the central structure portion of an apparatus according to this invention;

FIG. 5 is an enlarged sectional view taken along line V—V in FIG. 3;

FIG. 6 is a enlarged side view showing the relative position between the light seal circular plate of the light seal wheel and the dark box of the left side frame;

DESCRIPTION OF THE PREFERRED EMBODIMENTS

Figure 1:
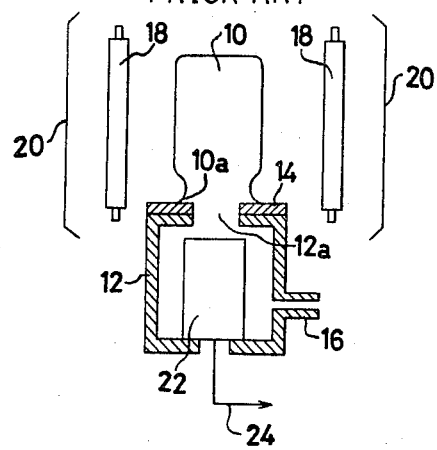
FIG. 1 is a schematic sectional view of the principal parts and structure of a conventional pinhole detection apparatus.
Figure 3:
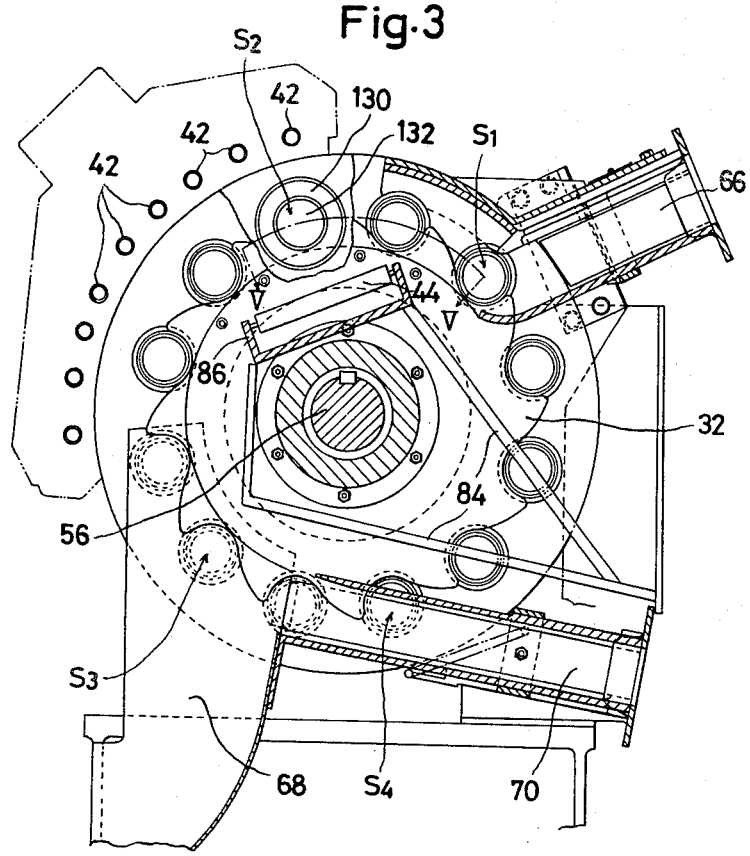
FIG. 3 is a partly cutaway vertical sectional view taken along line III—III in FIG. 2.
Figure 4:
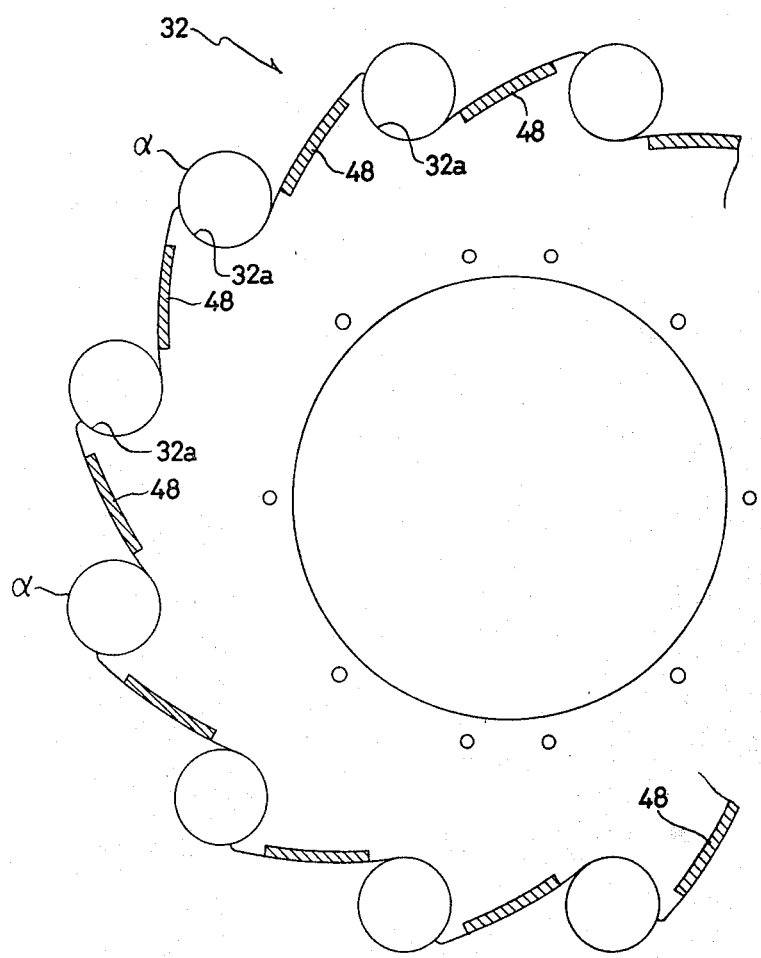
FIG. 4 is a partly cutaway side view of the star wheel.

Referring to FIGS. 2 and 3, in which one embodiment of this invention is illustrated, a rotary light tester (A) for continuously inspecting empty cans comprises a duplex star wheel of transparent acrylic and which includes circular-arc-shaped can receiving seats (32a) passing an empty can supply station (S1), a light detecting station (S2), a defective can discharge station (S3) and a good can discharge station (S4). The star wheel receives uncoated or unprinted empty cans (a) one by one just after the cans pass through the trimming operation. The receiving seats (32a) are provided on an outer periphery at equal intervals in the circumferential direction. A pusher holder wheel (40) which has a slide pusher (34) at equal intervals in the circumferential direction is operable to push a bottom end (a1) of an empty can (a) provided in the can receiving seat (32a) in the axial direction. The pusher holder (40) synchronously and rotatingly faces the star wheel (32) with the can receiving seat on the star wheel (32) located opposite a light seal wheel (38) which provides a light seal circular plate (36) thereon. The can receiving seats are at equal intervals in the circumferential direction. The can receiving seat receives the opening end ($\alpha2$) of the empty can ($\alpha$) pushed by the slide pusher (34). Upper and lower lights (42) (44) are disposed in the light detection station (S2) and irradiate all over the can ($\alpha$) passing therethrough, and a light detector (46) which is disposed at the position corresponding to the station (S2) detects light entering into the interior ($\alpha3$) of the can ($\alpha$) through the light seal circular plate (36) when the seal plate (36) is aligned with the detector (46). As illustrated in FIG. 4, plastic material (48) of a good sliding property is provided in the outer inclined surface between the receiving seats (32a) to make it easy to put a bright can ($\alpha$) having a bad sliding property into the seat (32a) and take it therefrom. As shown in FIG. 4, the can receiving seat (32a) is partially circular with the center of the partial circle coinciding with the center of a can disposed within the can receiving seat. A radial line passing through the center of the star wheel (32) and the center of the aforementioned partial circle defines an imaginary dividing line (not shown) which divides the can receiving seat into a first section which has a concave or partially circular configuration for receiving an empty can and a second section which encompasses the plastic material (48). The star wheel (32), the light seal wheel (38) and the pusher holder wheel (40) are axially fixed on a drive shaft (56) to be idlingly supported between both left and right side frames (52)(54) opposing each other on a base (50). The drive shaft (56) is driven by the transmission of drive torque of a motor (not shown) through a belt (64) from a reduction gear (58) equipped at one end thereof.

In this invention (A), the empty can supply opening (66) at the station (S1) supplies the can receiving seat (32a) with cans one by one passing them in accordance with rotation of the star wheel (32). The defective can discharge opening (68) of the station (S3) removes cans ($\alpha$) judged defective in the light detection station (S2) from the can receiving seat (32a) and discharges them outside the apparatus. The good can discharge opening (66) of the station (S4) removes cans ($\alpha$) judged good from the receiving seat (32a) and discharges them outside the apparatus.

In addition, in the drawings, (72) and (74) are respectively housing covers.

Figure 7:
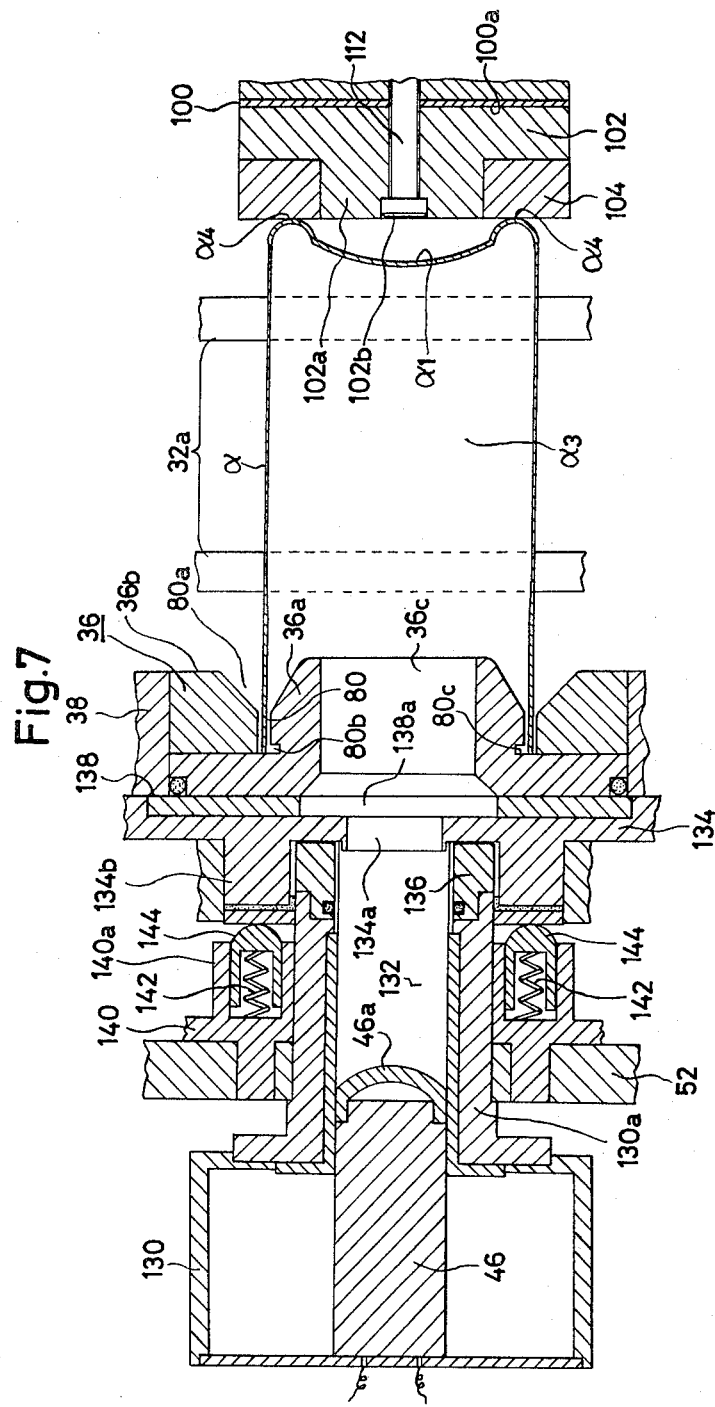
FIG. 7 is an enlarged central vertical sectional view illustrating an empty can being inspected in the detection station.

The light seal circular plate (36), as illustrated in FIGS. 5 to 7, consists of a combination of an inner holder (36a) and an outer holder (36b). The outer holder (36b) is screwed down through a plate (78) by a screw (76) to be easily able to replace the seal plate (36) with a new one and to maintain it clean. The light seal circular plate (36) has a conical introduction part (80a) in the entrance portion and a groove (80) communicating with a trap (80b) in the deepest portion thereof to make it easy to insert the open end ($\alpha2$) of the empty can ($\alpha$). The opening end ($\alpha2$) of the can ($\alpha$) is inserted until the bottom (80c) of the groove (80) during detection of pinholes. The light seal circular plate (36) is composed of harder materials than those of the can ($\alpha$) and therefore is not damaged by contacting the can ($\alpha$), such as superhard-substances, sintering ceramics, hard-facing-treated steel and so forth. The hard facing treatments are preferably, for example, nitriding treatment and metal or ceramics spray coating treatment.

Figure 8:
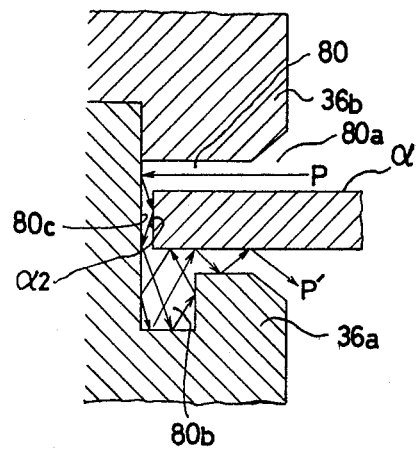
FIG. 8 is an explanatory view of the light leakage attenuation action in the groove of the light seal circular plate.

FIG. 8 shows the attenuation action of the amount of light leakage in the groove (80) of the light seal circular plate (36). Outer light (P), as illustrated in the embodiment of FIG. 11, penetrates into the clearance between the can ($\alpha$) and the groove (80). Outer light (P) is reflected at right angles to the bottom (80c) of the groove (80) and is leaked into the interior of the can from the clearance between the opening end ($\alpha2$) and the bottom (80c) of the groove (80). This leaked light is further directed to 90° with repeated reflections inside the bottom (80c) of the groove (80) and simultaneously remarkably attenuated, and then directed into the interior ($\alpha3$) of the can ($\alpha$) with repeated reflections. Synergism of both the groove (80) and the trap (80b) produces the great attenuation action. Therefore, the amount of leaked light (P') into the interior ($\alpha3$) of the can ($\alpha$) is greatly reduced and is much smaller than that of detection light through pinholes. Hence it is possible to neglect the amount of light leakage.

In addition, it is possible to reduce the coefficient of reflection by utilizing black non-luster on the surface of the groove (80) and the trap (80b). Therefore it is preferable that the groove (80) and the trap (80b) are constituted of black sintering ceramics, which reduces the amount of light leakage into the interior of the can.

As shown in FIGS. 2 and 3, the upper lights (42) are disposed along the inner surface of a circular-arc-shaped reflector (82) provided above the station (S2) at desired intervals in the circumferential direction. On the other hand, the lower lights (44) are disposed on a bracket (86) with the supporting member (84) below the station (S2) to irradiate passing empty can ($\alpha$) during inspection.

As illustrated in FIG. 2, the slide pusher (34) is inserted to reciprocally move in the axial direction in a guide sleeve (88) aligned with each can receiving seat (32a) on the outer periphery of the pusher holder wheel (40). Reciprocative movement and rotation of the slide pusher (34) are limited by a sliding key (90). A pair of can followers (92) (94) are rotatingly disposed in the back projecting portion and sandwiches a cam projecting portion (96a) on an outer periphery of a circular plate cam (96) of which the drive shaft (56) pierces through the center thereof and which extends from a right frame (54). The slide pusher (34) rotating together with the pusher holder wheel (40) moves forward to the limited position at the time just before passing the station (S2) by a drawing of the cam projecting portion (96a) sandwiched between the cam followers (92) (94). As illustrated in FIGS. 2 and 5, a head (106) constitutes a transparent pusher face (102) fixed over a tip of a block part (98) with a shim (100) having a reflection surface (100a) between, and a circular transparent rubber ring (104) of natural rubber is provided on an outer peripheral surface of a central projecting portion (102a) of the pusher face (102) instead of a spring to contact the bottom end rim ($\alpha4$) of the can ($\alpha$) to prevent deformation and to cope with difference of height among cans ($\alpha$) after the trimming operation. The head (106) is movably provided inside an opening (110a) of a side guide plate (110) fixed to a free end of an arm (108) projecting from the pusher holder wheel (40). In the center projecting portion (102a), a nozzle opening (102b) is provided to vacuously hold the bottom end ($\alpha1$) of the can ($\alpha$) in the station (S1) through the station (S4) and to blow the bottom end ($\alpha1$) of defective cans ($\alpha$) and remove them from the can receiving seat (32a).

Figure 9:
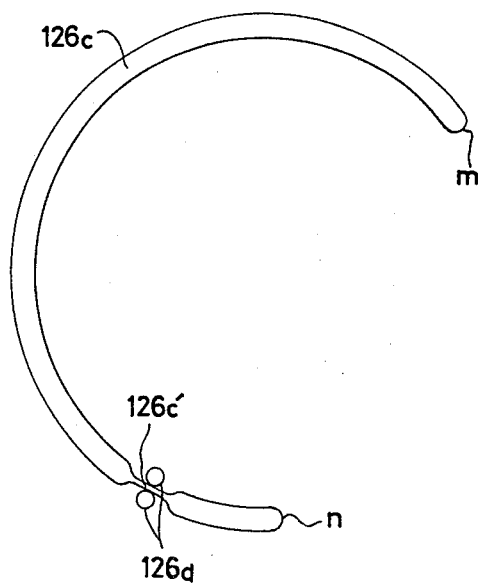
FIG. 9 is a plan view of the vacuum groove and the pressure aperture in the mediation plate.

The nozzle opening (102b) communicates with an attachment port metal fixture (114) by passing through the nozzle (112) through the shim (100), the pusher face (102) and the tip block part (98). The port fixture (114) is connected through a tube (122) to an attachment port metal fixture (120) disposed in an upper end opening (118a) of an L-shaped aperture (118) bored in an attachment circular plate (116) on one side of the pusher holder wheel (40). An arm (124) projecting from one side of the circular plate cam (96) faces against the circular plate (116) and is connectively inserted into a muzzle (126a). A vacuum groove (126c) is formed along a circular arc of about 240° extending from the empty can supply station (S1) to the good can discharge station (S4), as shown in FIG. 9, on a sliding surface (126b) of a mediation plate (126) which is pressed into contact with the circular plate (116) with elastic force by a compressed coil spring (128) wrapped around the arm (124). The lower end opening (118b) of the L-shaped aperture (118) opposed the groove 126. Pressure openings (126d) provided in both sides of an isthmus (126c') corresponding to the defective can discharge station (S3). The vacuum groove (126c) communicates with the vacuum source (not shown), and the pressure openings (126d) are coupled with the atmospheric pressure source (not shown) only when a defective can judging signal is transmitted from the light detector (46) with delay.

As illustrated in FIGS. 5 and 7, the light detector (46) has a detection end (46a) within a window aperture (132) of a dark box (130) passing through and fixed to an upper portion of a left side frame (52). The light detector is fitted movably in the axial direction into window opening of member (136) fixed at the tip of the window aperture (132) at window opening receipt cylinder portion (134b) which circularly projects out at equal intervals in the circumferencial direction of the face plate (134) and pierces a through-aperture (134a) at the center thereof. The light detector (46) is disposed freely matching the mutual axis with an inside aperture (36c) of the light seal circular plate through a middle aperture (138a) of a sliding ring (138) provided in front of the face plate (134) surrounding the through-aperture (134a). The face plate (134) and the sliding ring (138) are always contacted with pressure contact with the respective sliding face of the light seal wheel (38) and light seal circular plate (36) by pressing the back of the window opening receiving cylinder portion (134b) of the face plate (134) by a pusher (144) with the elastic force of compression coil springs (142) housed in the ring projecting portion (140a) of the back-up plate (140) fixed to the left side frame (52) through the window aperture (130a) of the dark box (130).

Also the face plate (134) and the sliding ring (138) always contact, with pressure contact, the respective sliding face of the light seal wheel (38) and light seal circular plate (36) by pressing the back of window opening receiving cylinder (134b) contacting only another window opening (136) by the pusher (44) with the elastic force of the compression coil springs (142) housed in the ring projecting parts (140a) of the back-up plate (140).

In this invention constituted as described above initially starting of a motor (not shown) actuates the drive shaft (56) at a fixed speed through a belt (64), a pulley (62), and the reduction gear (58) before the inspection work of the empty can (a) starts.

The can (a) fed from the empty can supply opening (66) passes one after another to one of the can receiving seats (32a) of the star wheel (32). The slide pusher (34) in the backward limited position advances along the side guide plate (110) by the cam action of the circular plate cam (96), and simultaneously the advanced slide pusher (34) contacts the head (106) thereof with the bottom end (a1) of the can (a) and begins to push it in the axial direction. Then the nozzle opening (102b) of the head (106) vacuously holds the bottom end (a1) of the can (a) when the lower end opening (118b) of the L-shaped aperture (118) begins to contact the end (m) of the vacuum groove (126c) of the mediation plate (126).

In parallel with that, the opening end (a2) of the can (a) is inserted into the introduction portion (80a) of the light seal circular plate (36) of the light seal wheel (38) with the slide pusher (34) advancing, and contacts the groove bottom (80c) of the seal circular plate (36). The slide pusher (34) is in the forward limited position at the time just before reaching the station (S2).

When the can (a) on the star wheel (32) comes in the station (S2) irradiated by the upper and lower lights (42) (44), coincidence of the inside aperture (36c) of the light seal circular plate (36) with the middle aperture (138a) of the sliding ring (138) equipped at the tip of the dark box (130) enables the light detector (46) to detect transit-leaked light entering from pinholes to the interior (a3) of the can (a) through the inside aperture (36c) of the light seal circular plate (36). At this time, the detector (46) outputs a defective can judging signal through the delay electric circuit (not shown) only when the amount of leakage exceeds the reference level.

After the can (a) on the rotating star wheel (32) passes the station (S2), the slide pusher (34) begins to withdraw by the cam action of the circular plate cam (96) and is in the position that the opening end (a2) of the can (a) pulls perfectly out of the introduction portion (80a) of the groove (80) of the light seal circular plate (36) at the time just before reaching the station (S3). When the can (a) comes in the station (S3), coincidence of the low end opening (118b) of the L-shaped aperture (118) of the attachment circular plate (116) with the pressure opening (126d) of the mediation plate (126), in case the can (a) has been judged defective by the light detector (46), enables pressure air from the nozzle opening (102b) of the slide pusher (34) to remove the bottom end (a1) of the can (a) from the head (106) with the pressure air supply (not shown) and the pressure opening (126d) communicating with each other on delay receipt of the defective can judging signal. Then the defective can (a) falls off from the can receiving seat (32a) to the defective can discharge outlet (68) by its own weight and finally is discharged out of the apparatus (A).

As for the can (a) having been judged good in the station (S2), the can (a) passes the station (S3) with the bottom end (a1) held in the can receiving seat (32a). Then, in the station (S4), the vacuum absorption force is reduced down to 0 after the lower end opening (118b) of the L-shaped aperture (118) of the attachment circular plate (116) passes the end (n) of the vacuum groove (126c) of the mediation plate (126). The can (a) falls off from the can receiving seat (32a) to the good can discharge outlet (70) by its own weight and finally is discharged out of the apparatus (A).

This apparatus continuously judges the cans (a) defective or not and discharges them during a rotation of the star wheel (32).

This invention, as aforementioned, is characterized in that insertion of the opening end (α2) of the empty can (α) into the groove (80) provided in the high hardness light seal circular plate (36) reduces the amount of light leakage from the clearance between the opening end (α2) and the light seal circular plate (36) to a substantially neglectable amount with the light attenuation action of the groove (80). Namely, the amount of permissible leaked light is effectively reduced without perfectly shutting out penetration light into the clearance between the opening end (α2) and the seal plate (36). Therefore, there is no case where the strong tight press of the opening end (α2) having a very thin end surface of about 0.17 mm, which is difficult to deal with just after the trimming work, damages the light seal plate (14) of a conventional rubber packing. Further, it is possible to detect trimming defective cans which have shorter finish height. In addition, the detection of uncoated or unprinted bright can makes it possible to detect pinholes of 25μ diameter or below with high accuracy.

As aforementioned, this invention can utilize good materials with wear resisting property and high hardness materials in the light seal plate and prolong remarkably the maintenance and replacement term without wearing of the light seal plate since the contact pressure is so small. Especially, not considering the wear of the light seal plate, the pinhole detection is made with no roundness of the opening end processed before coating or printing, therefore the occurrence of the error detection resulting from covering pinholes with coatings or print inks can be certainly prevented. In addition, since pinholes are detected before coating and printing, the contamination of the mandrel by penetration of coatings or print inks through pinholes into the interior of the can is effectively prevented.

As above mentioned, this invention provides a pinhole detection apparatus which can be continuously used for a long time and is available to broadly apply inspection in various can manufacturing and other processing.

In addition, this invention is able to automatically classify defective and goods cans with high accuracy with a high efficient working ratio and is provides for the reduction of labor and cost and results in high quality goods.

What we claim is:

1. A rotary light tester for continuously inspecting empty cans for defects comprising a star wheel means having a plurality of can receiving seat means for accepting empty cans one by one, an empty can supply station, a light detection station, a defective can discharge station and a good can discharge station, said stations being disposed about the periphery of said star wheel means, said can receiving seat means having a first section and a second section with the dividing line between said first and second sections being a radial line passing through the center of said star wheel means and through the center of a can in said seat means, said first section having a concave configuration for receiving said can, said second section having a configuration differing from the configuration of said first section and having sliding means for facilitating exiting of said can from said seat means, said sliding means comprising an insert on said second section, said insert being made of a plastic material having the property of facilitating sliding of said cans on said insert, slide pusher means operable to push a bottom end of an empty can in said can receiving seat means in an axial direction, said slide pusher means having a head, vacuum and vacuum release means having a nozzle opening in said head for vacuously supporting said bottom end of the empty can from said empty can supply station through said good can discharge station and for releasing said vacuum when a defective can is to be discharged in said defective can discharge station, said vacuum and vacuum release means comprising a non-rotatable mediation plate having a flat surface disposed perpendicular to the axis of said star wheel means, a vacuum groove disposed in said flat surface, said vacuum groove having the configuration of a part of a circle with a beginning and an end with the beginning of the vacuum groove being disposed generally aligned with said empty can supply station and the end of said vacuum groove being generally aligned with said good can discharge station, said slide pusher means having a circular plate with a plate surface disposed perpendicular to the axis of said star wheel, said circular plate having a vacuum opening, conduit means in said slide pusher means extending between said vacuum opening and said nozzle opening, said vacuum opening being adapted to communicate with said vacuum groove in said mediation plate to provide vacuum to said nozzle opening for vacuously supporting said bottom end of the empty can from said empty can supply station through said good can discharge station, said vacuum groove having a narrow section located at a position generally aligned with said defective can discharge station, air pressure openings in said mediation plate adjacent to said narrow section of said vacuum groove, said vacuum opening in said circular plate being constructed and arranged to communicate with said air pressure openings adjacent to said narrow section of said vacuum groove such that air pressure from said air pressure openings is thereby supplied to said vacuum opening in said circular plate and thence to said nozzle opening to release a can from said seat means when the latter is in said defective can discharge station, biasing means biasing said mediation plate in an axial direction toward said circular plate to provide biasing and sliding contact between said mediation plate and said circular plate on said slide pusher means, light source means for irradiating the can passing through said light detection station, light seal plate means for sealing light entering into the interior of the can, and light detector means for detecting light generating through defects in the can, said defective can discharge station being disposed at a discharge position offset from a vertical line passing through the center of said star wheel means, said vacuum and vacuum release means applying air pressure from said air pressure openings to release a defective can in said defective can discharge station in response to detection of a defective can by said light detector means, said seat means being constructed and arranged such that when said vacuum is released at said defective can discharge station, the defective can therein is free to fall by its own weight from said seat means into said defective can discharge station.

2. A rotary light tester according to claim 1, wherein said first section of said receiving seat means has a generally U-shaped configuration and said second section has a non-concave configuration.

3. A rotary light tester according to claim 2, wherein said second section has a convex configuration.

4. A rotary light tester according to claim 1, wherein said seat means is constructed and arranged such that when the seat means is in said defective can discharge station, the can in the seat means in said defective can discharge station is free to fall straight down by gravity.

5. A rotary light tester according to claim 1, wherein said vacuum groove extends about 240 degrees.

6. A rotary light tester according to claim 1, wherein said slide pusher means comprises a pusher block, a transparent pusher face member fixed to said pusher block, a shim having a reflective surface disposed between said pusher block and said pusher face member, and a transparent rubber annular member disposed on said pusher face member and adapted to contact the outer rim of a can as the latter is disposed in said seat means, said rubber annular member having sufficient resiliency to provide for handling cans of varying longitudinal lengths, said slide pusher means further comprising a cam device for longitudinally advancing and withdrawing said pusher block, and a fixed cam ring engaged by said cam device, said pusher block and said cam device being fixed to one another to longitudinally advance and withdraw the same distance.

7. A rotary light tester according to claim 1, wherein said light seal plate means has a receiving groove for receiving the open end of the can.

* * * * *